United States Patent

Noonan et al.

[11] Patent Number: 6,049,014
[45] Date of Patent: Apr. 11, 2000

[54] PROCESS FOR THE MANUFACTURE OF TETRABROMOBISPHENOL-A WITH CO-PRODUCTION OF N-PROPYL BROMIDE

[75] Inventors: Anne P. Noonan, Lafayette; Stephen C. Scherrer, West Lafayette, both of Ind.

[73] Assignee: Great Lakes Chemical Corporation, West Lafayette, Ind.

[21] Appl. No.: 09/026,262

[22] Filed: Feb. 19, 1998

Related U.S. Application Data

[60] Provisional application No. 60/038,440, Feb. 19, 1997.

[51] Int. Cl.$^7$ .................................................. C07C 39/16
[52] U.S. Cl. ......................... 568/725; 568/726; 568/720; 568/728; 568/729
[58] Field of Search ..................................... 568/725, 728, 568/729, 720, 726; 528/98; 524/739

[56] References Cited

U.S. PATENT DOCUMENTS

| | | | |
|---|---|---|---|
| 3,029,291 | 4/1962 | Dietzler | 260/619 |
| 3,234,289 | 2/1966 | Hennis | 260/619 |
| 4,059,638 | 11/1977 | Krimm et al. | 568/640 |
| 4,451,675 | 5/1984 | Bounds | 568/726 |
| 4,701,568 | 10/1987 | McKinnie et al. | 568/726 |
| 4,717,760 | 1/1988 | Parker et al. | 528/98 |
| 4,777,297 | 10/1988 | Ogawa et al. | 568/33 |
| 4,990,321 | 2/1991 | Sato et al. | 423/486 |
| 5,008,469 | 4/1991 | Eguchi et al. | 568/722 |
| 5,059,726 | 10/1991 | Eguchi et al. | 568/726 |
| 5,138,103 | 8/1992 | Eguchi et al. | 568/726 |
| 5,237,112 | 8/1993 | LaRose | 568/726 |
| 5,283,375 | 2/1994 | McKinnie et al. | 568/726 |
| 5,446,212 | 8/1995 | Sanders et al. | 568/726 |
| 5,475,153 | 12/1995 | Armstrong | 568/726 |
| 5,527,971 | 6/1996 | McKinnie | 568/726 |

FOREIGN PATENT DOCUMENTS 706433  3/1965  Canada .

*Primary Examiner*—Ralph Gitomer
*Assistant Examiner*—Marjorie A. Moran
*Attorney, Agent, or Firm*—Woodard, Emhardt, Naughton, Moriarty & McNett Patent and Trademark Attorneys

[57] ABSTRACT

A process for producing n-propyl bromide during the bromination of bis- or trisphenols uses non-aqueous n-propanol as the bromination solvent, providing salable yields of n-propyl bromide to accompany the brominated bisphenol or trisphlenol.

20 Claims, No Drawings

PROCESS FOR THE MANUFACTURE OF TETRABROMOBISPHENOL-A WITH CO-PRODUCTION OF N-PROPYL BROMIDE

The present application claims the benefit of U.S. patent application Ser. No. 60/038,440, filed on Feb. 19, 1997.

FIELD OF THE INVENTION

The present invention relates generally to the production of bis- and trisphenols; and more particularly to a process for the production of tetrabromobisphenol-A with the co-production of salable n-propyl bromide.

BACKGROUND OF THE INVENTION

Tetrabromobisphenol-A (TBBPA) is the largest volume brominated flame retardant in the world. Its widespread utility in reducing risks of fire from certain plastics is in part due to its economy. The low manufacturing cost is, in turn, due to processes in which salable methyl bromide (a valuable soil fumigant) is co-produced with the TBBPA.

Methyl bromide is now suspected as being a factor in the depletion of the earth's ozone layer. Severe restrictions on the sale of methyl bromide are imminent. To maintain low manufacturing costs, it would therefore be desirable to co-produce a different salable chemical with the TBBPA.

N-propyl bromide has gained interest in recent years as a degreasing solvent in the precision cleaning industry. Due to the present market that exists and growth projections for that market, a method to economically produce high quality n-propyl bromide is desired. The economics of both TBBPA and n-propyl bromide production for sale are both improved using the co-production techniques outlined herein.

Prior art methods of producing TBBPA with the concomitant reduction of methyl bromide typically involve brominating bisphenol A (BPA) in the presence of an aqueous $C_1$ to $C_4$ alcohol. Although an aqueous n-propanol solvent system has been utilized to form TBBPA, it has been shown to produce a TBBPA product of lower yield that is more difficult to wash compared to a TBBPA product formed in an aqueous ethanol solvent system.

Other prior art methods have utilized either an aqueous alcohol or a non-polar solvent in combination with an oxidizing agent to reduce the amount of alkyl bromides formed. However, none of the prior art found to date discloses the use of non-aqueous n-propanol as the sole solvent and that reaction conditions may be adjusted to maximize the production of salable n-propyl bromide.

A need therefore exists for a process for making TBBPA in which the economics support the continued worldwide use of this valuable product, but in which potentially harmful methyl bromide is not generated. The present invention addresses that need.

SUMMARY OF THE INVENTION

Briefly describing one aspect of the present invention, there is provided an improved method for producing n-propyl bromide during the bromination of bis- or trisphenols. In one aspect of the invention, non-aqueous n-propanol is used as the bromination solvent, providing salable yields of n-propyl bromide to accompany the brominated bisphenol or trisphenol.

It is an object of the invention to provide an economical process for the production of bis(dibromophenols) or brominated trisphenols in which salable n-propyl bromide is co-produced.

Further objects and advantages of the present invention will be apparent from the following description.

DESCRIPTION OF THE PREFERRED EMBODIMENT

For the purposes of promoting an understanding of the principles of the invention, reference will now be made to preferred embodiments and specific language will be used to describe the same. It will nevertheless be understood that no limitation of the scope of the invention is thereby intended, such alterations and further modifications in the illustrated embodiments, and such further applications of the principles of the invention as illustrated therein, being contemplated as would normally occur to one skilled in the art to which the invention relates.

The invention provides a method for the co-production of both high quality n-propyl bromide, bis(dibromophenols) and brominated trisphenols by combining non-aqueous n-propanol and a bisphenol or trisphenol in the presence of bromine.

As used herein, the term "bisphenol" includes, but is not limited to, alkylidenediphenols such as 4,4'-methylenediphenol, 2,2' methylenediphenol (bisphenol F), 4,4'-ethylidenediphenol, 4,4'-isopropylidenediphenol (bisphenol A), 4,4'-isobutylenediphenol, 4,4'-secbutylenediphenol and 4,4'-dihydroxydiphenyl sulfone (bisphenol S). These bisphenols are commercially available or readily produced by those skilled in the art of this invention. For example, 4,4'-isopropylidenediphenol may be produced from phenol and acetone, as described in U.S. Pat. No. 2,468,982 to Jenson, incorporated herein by reference. Moreover, the process is also applicable to biphenol, and hydroxyphenols, including resorcinol. However, of the alkylidenediphenols, BPA is a most preferred reactant.

The invention is preferably practiced by first adding a bisphenol or a trisphenol to non-aqueous n-propanol to form a mixture which is preferably between about 2% and about 70% by weight bisphenol or trisphenol and most preferentially between about 20% and about 40% by weight bisphenol or trisphenol for batch processes. The starting bisphenol or trisphenol concentration may affect the co-product bis (dibromophenol) or brominated trisphenol quality and yield.

Preferably, only water incidental to the n-propanol solvent and bisphenol or trisphenol is present during the bromination reaction. For example, in the preferred embodiments the reaction mixture contains less than 10% water during the bromination reaction, with the more preferred embodiments having less than 8% water, and the most preferred embodiments having less than 5% water. In other embodiments, substantially no water is present during the bromination reaction. Hereinafter, unless otherwise noted "non-aqueous" means less than 10% water.

When a bisphenol is a reactant, preferably between about 4.0 moles to about 4.5 moles of bromine per mole of bisphenol charged and further preferably between about 4.0 moles to about 4.2 moles of bromine per mole of bisphenol charged is added to the bisphenol and non-aqueous n-propanol solution. When a trisphenol is a reactant, preferably between about 5 moles to about 7 moles of bromine permole of trisphenol charged is added to the trisphenol and non-aqueous n-propanol solution. The reaction temperature is preferably maintained at less than 40° C. and further preferably at less than 25° C. during the addition of bromine. External cooling is needed to allow for the timely addition of the bromine charge.

The bromination mixture is allowed to hold at specified temperatures and for specified periods of time during which time the bromination of the alkylidene bis(dibromopheniol) and co-production of n-propyl bromide continues. The hold times and temperatures can be adjusted to control n-propyl bromide quantity and bis(dibromophenol) or brominated trisphenol quality. In general, higher temperatures and longer hold times increase n-propyl bromide production while resulting in less bis(dibromophenol) and brominated trispheriol yield and lower bis(dibromophenol) and brominated trisphenol quality. The hold period is between about 0 hours to about 24 hours and is most preferentially between about 1 hour and about 16 hours. The hold temperatures are preferably between about 10° C. to about 90° C.

During the hold period and preferably at the end of the hold period, the n-propyl bromide formed may be, in part or in whole, removed from the reaction mixture arid collected using distillation techniques or other means familiar to those skilled in the art. For example, n-propyl bromide can be removed as a vapor from the reactor by application of a vacuum to the reactor, heating the reaction mixture to temperatures exceeding the boiling point of n-propyl bromide, or by subsurface sparging of an inert gas through the reaction mixture. Once removed from the reactor, the n-propyl bromide vapor is condensed. In the present process, simple distillation techniques can be used to obtain n-propyl bromide with an assay greater than 95%.

The co-product bis(dibromophenol) or brominated trisphenol is recovered after the broinination of the bispheniol or trisphenol has been completed, the desired hold period has occurred, and n-propyl bromide has been in part or in whole, and optionally, removed from the reactor. The method of recovery of the bis(dibromophenol) or brominated trisphenol is not key to the invention, but in the present process involves adding water to the reaction mass to induce and/or complete precipitation of the product from solution. In the present process the water is added after the bromination is substantially complete and can be added before or after the hold period and preceding or following the removal, if pursued, of n-propyl bromide from the reactor. Prior to the water addition, the reaction mass may be cooled and the water of precipitation warmed in order to manipulate the character of the product crystals. This may be important in order to optimize parameters such as filtration rates, wash efficiency, and product assay.

Water charged to the reaction mass may have the added effect of reducing the level of n-propyl bromide formation. Water added early in the hold period will result in less n-propyl bromide than water added later in the hold period. It is important to balance the water addition amounts and methodology with the experimental objectives for bis (dibromophenol) or brominated trisphenol quality with n-propyl bromide quantities. Other isolation processes might use different non-solvents to force precipitation, or could rely on concentrating the reaction mass by stripping some of the propanol and filtering the solids from the concentrate. When the bisphenol is BPA, the co-product TBBPA formed in the present process has a purity greater than 95% as measured by liquid chromatography techniques.

Regardless of the method of solids isolation, the solids may then be washed to remove residual solvent, acidity, or unreacted bromine. Agents may be added to the washes to improve product quality.

Furthermore, or as an alternative to recovery of n-propyl bromide during the hold period, n-propyl bromide can be recovered from the reaction mother liquor by applying distillation techniques or by other means, such as, but not limited to, extraction techniques as are known to those skilled in the art.

The process may be carried out in either batch or continuous fashion. When run continuously, a more dilute solution would be preferred. In any case, the bromination exotherm must be balanced against product quality.

The non-aqueous n-propanol may contain lesser amounts of non-aqueous solvents such as methylene chloride, ethylene dichloride, or chlorobenzene, but it is preferred that it be used undiluted.

Reference will now be made to specific examples using the processes described above. It is to be understood that the examples are provided to more completely describe preferred embodiments, and that no limitation to the scope of the invention is intended thereby.

EXAMPLE 1

Typical Reaction with N-Propyl Bromide Removal

A two-liter round bottom flask was equipped with a condenser, a stirrer, a thermometer and a dropping funnel. The flask was charged with 515 grams of non-aqueous n-propanol and 228 grams of BPA. 650 grams of bromine was added to the stirred reactor contents over 1 hour at temperatures not exceeding 35° C. Upon completion of the bromine addition, the reaction vessel contents were heated to reflux temperatures which initially were 79° C. During the reflux period, a white slurry formed in the reaction vessel. After three hours at reflux, the pot was sampled and found to contain 2.16 grams n-propyl bromide formed per gram BPA charged to the reaction by gas chromatography. A portion of the n-propyl bromide was stripped from the reaction vessel using distillation techniques. 233 grams of distillate, which was 95% rich in n-propyl bromide, was collected during the strip.

The TBBPA was precipitated using standard laboratory techniques known to those skilled in the art and was removed from the reaction mixture by filtration at 60° C. using a Buchner funnel. The co-product was washed and dried and found to have an assay of 99% TBBPA by liquid chromatography.

EXAMPLE 2

Low BPA Concentration 721 grams of non-aqueous n-propanol and 80 grams of BPA were placed in a two-liter reaction vessel equipped with a condenser, a stirrer, a thermometer and a dropping funnel. 228 grams of bromine was added to the stirring reactor contents in less than 2 hours at temperatures not exceeding 35° C. Upon completion of the bromine addition, the reaction vessel contents were heated to reflux temperatures which initially were 86° C. During the reflux period, a light yellow slurry formed in the reaction vessel. After three hours at refluix, distillation techniques were used to strip n-propyl bromide from the reaction vessel. 145 grains of distillate containing 59% n-propyl bromide was collected.

The TBBPA was precipitated using standard laboratory techniques known to those skilled in the atrt and was removed from the reaction mixture by filtration at 10° C. using a Buchner funnel. The co-produlct was wvashed and dried. The TBBPA collected had an assay of 98%.

EXAMPLE 3

High N-Propyl Bromide and TBBPA Yields 787 grams of non-aqueous n-propanol and 228 grams of BPA were placed in a two-liter reaction vessel equipped with a condenser, a stirrer, a thermometer and a dropping funnel. Thereafter, 655 grams of bromine were added to the stirred reactor contents in less than one-half hour at temperatures not exceeding 25° C. Upon completion of the bromine addition, the reaction vessel contents were heated to reflux which was initially 90° C. After two and one-half hours at reflux, the reactor contents were sampled and found to contain 1.47 grams n-propyl bromide per gram BPA charged to the reactor by gas chromatography analysis.

The TBBPA co-product was precipitated from the reaction mixture using standard laboratory techniques known to those skilled in the art and then removed from the reaction mixture by filtration at 30° C. using a Buchner funnel. The TBBPA was washed and dried. The TBBPA collected had a chemical yield of 95% and an assay of 99% by liquid chromatography analysis.

EXAMPLES 4–7 AND COMPARATIVE EXAMPLE 8

TABLE 1

| Example | Water Present grams | Non-aqueous n-Propanol added grams | Hold temperature ° C. | n-PrBr[1] formed per BPA charged gram/gram | TBBPA Assay % |
|---|---|---|---|---|---|
| 4 | 0 | 370 | 60 | 0.83 | 98 |
| 5 | 0 | 370 | 75 | 1.19 | 98 |
| 6 | 0 | 450 | 67.5 | 0.95 | 97 |
| 7 | 0 | 300 | 67.5 | 0.87 | 94 |
| 8 Comp. | 300[2] | 370 | 67.5 | 0.04 | 99 |

[1] n-PrBr = n-propyl bromide
[2] water was charged with non-aqueous n-propanol and BPA prior to bromine addition Examples 4–8 shown in Table 1 share the following parameters:

200 gram BPA charge;

585 gram bromine addition at about 20° C. in about 2 hour;

About a 2 hour hold period at the hold temperature indicated;

In-situ measurement of the n-propyl bromide; and

TBBPA precipitation and isolation using typical lab techniques.

Examples 4 and 5 in Table 1 illustrate how modifications in the reaction temperature can affect the quantity of n-propyl bromide formed.

Examples 6 and 7 reflect the fact that the amount of non-aqueous n-propanol charged to the reaction did not affect n-propyl bromide production but has affected the co-product TBBPA quality.

Example 8 is a comparative example of the negative impact water can have on n-propyl bromide production. In experiment 8, where the n-propanol concentration in water is 55%, a significant reduction in the level of n-propyl bromide formed during the reaction and hold period is noted when compared to the non-aqueouis Examples 4–7.

EXAMPLE 9

Production of Propyl Bromide from a Reaction Mother Liquor

A two liter round-bottom flask was equipped with a thermometer, a stirrer and an insulated 10" column attached to a condenser. The flask was charged with 761 grams of typical n-propyl alcohol/tetrabromobisphenol-A mother liquor. The mother liquor contained 20 grams of propyl bromide as determined by gas chromatography. The material in the flask was heated with agitation. Collection of distillate started at a 61° C. overhead temperature. The distillation was continued for 6 hours until an overhead temperature of 91° C. was reached. A total of 538 grams distillate was collected. The distillate was found to contain 218 grams of n-propyl bromide by gas chromatography. The n-propyl bromide produced over the course of the distillation represented 0.99 grams n-propyl bromide for every gram BPA charged in the bromination reaction.

While the invention has been illustrated and described in detail in the foregoing description, the same is to be construed as illustrative and not restrictive in character, it being understood that only the preferred embodiment has been shown and described and that all changes and modifications that come within the spirit of the invention are desired to be protected.

What is claimed is:

1. A method for co-producing n-propyl bromide and brominated bisphenols, said method comprising:
   a) dissolving a bisphenol in non-aqueous n-propanol to form a reaction solution;
   b) contacting the reaction solution with bromine to form brominated bisphenol and n-propyl bromide;
   c) recovering the formed n-propyl bromide; and
   d) recovering the brominated bisphenol.

2. The method of claim 1 wherein said dissolving step comprises dissolving bisphenol in non-aqueous n-propanol to form a reaction solution that is 2% to 70% by weight bisphenol.

3. The method of claim 1 wherein said method further comprises heating the reaction solution after bromine addition to a temperature of between 10° C. and 90° C. to promote the formation of brominated bisphenol.

4. The method of claim 3 wherein said method further comprises maintaining the temperature of the heated reaction solution eithin the range of between 10° C. and 90° C. for a period of between 0 and 24 hours.

5. The method of claim 3 wherein said method further comprises maintaining the temperature of the heated reaction solution within the range of between 10° C. and 90° C. for a period of between 1 and 16 hours.

6. The method of claim 1 wherein said contacting step comprises contacting the reaction solution with a stoichiometric amount of bromine to form brominated bisphenol.

7. The method of claim 1 wherein the bisphenol is an alkylidenediphenol.

8. The method of claim 7 wherein the alkylidenediphenol is bisphenol A.

9. The method of claim 8 wherein said contacting step comprises contacting the reaction solution with 4 to 4.5 moles of bromine per mole of bisphenol A.

10. The method of claim 1 wherein said bisphenol is bisphenol S.

11. The method of claim 1 wherein the bromine is added to the reaction mixture over a period of less than about 2 hours.

12. The method of claim 1 wherein the reaction solution is maintained at a temperature less than about 40° C. during said adding bromine.

13. A method for co-producing n-propyl bromide and brominated trisphenols, said method comprising:
   a) adding a trisphenol to non-aqueous n-propanol to form a reaction mixture;
   b) contacting the reaction mixture with bromine to form brominated trisphenol and n-propyl bromide;
   c) recovering the formed n-propyl bromide; and
   d) recovering the brominated trisphenol.

14. The method of claim 13 wherein said adding step comprises adding trisphenol in non-aqueous n-propanol to form a reaction mixture that is 2% to 70% by weight trisphenol.

15. The method of claim 13 wherein said method further comprises heating the reaction mixture after bromine addition to a temperature of between 10° C. and 90° C. to promote the formation of brominated trisphenol.

16. The method of claim 15 wherein said method further comprises maintaining the temperature of the heated reaction mixture within the range of between 10° C. and 90° C. for a period of between 0 and 24 hours.

17. The method of claim 15 wherein said method further comprises maintaining the temperature of the heated reaction mixture within the range of between 10° C. and 90° C. for a period of between 1 and 16 hours.

18. The method of claim 13 wherein said contacting step comprises contacting the reaction solution with a stoichiometric amount of bromine to form brominated trisphenol.

19. The method of claim 13 wherein the bromine is added to the reaction mixture over a period of less than about 2 hours.

20. The method of claim 13 wherein the reaction mixture is maintained at a temperature less than about 40° C. during said adding bromine.

* * * * *